United States Patent [19]

Edwards et al.

[11] Patent Number: 5,470,309

[45] Date of Patent: Nov. 28, 1995

[54] MEDICAL ABLATION APPARATUS UTILIZING A HEATED STYLET

[75] Inventors: Stuart D. Edwards, Los Altos; Ronald G. Lax, Grassvalley; Ingemar H. Lundquist, Pebble Beach; Hugh R. Sharkey, Redwood City, all of Calif.

[73] Assignee: Vidamed, Inc., Menlo Park, Calif.

[21] Appl. No.: 180,512

[22] Filed: Jan. 12, 1994

Related U.S. Application Data

[63] Continuation-in-part of Ser. No. 929,638, Aug. 12, 1992, abandoned, Ser. No. 12,370, Feb. 2, 1993, Pat. No. 5,370,675, Ser. No. 62,364, May 13, 1993, and Ser. No. 61,647, May 13, 1993, Pat. No. 5,421,819.

[51] Int. Cl.$^6$ .................................................. A61B 17/39
[52] U.S. Cl. ........................................................... 604/22
[58] Field of Search ............................ 604/22, 164, 280, 604/19–20, 53; 606/1–4, 11–17, 39, 45, 32; 601/2; 607/96, 101, 113, 102, 115, 116, 138, 156

[56] References Cited

U.S. PATENT DOCUMENTS

| | | |
|---|---|---|
| 32,066 | 1/1886 | Leveen . |
| 1,879,249 | 9/1932 | Hansaker ................................ 604/280 |
| 1,950,788 | 3/1934 | Ewerhardt et al. . |
| 1,968,997 | 8/1934 | Drucker . |
| 2,008,526 | 7/1935 | Wappler et al. . |
| 2,022,065 | 11/1935 | Wappler . |

(List continued on next page.)

FOREIGN PATENT DOCUMENTS

| | | |
|---|---|---|
| 10858/92 | 8/1992 | Australia . |
| 219216A1 | 4/1987 | European Pat. Off. . |
| 0370890 | 5/1990 | European Pat. Off. . |
| 0453071 | 10/1991 | European Pat. Off. . |
| 0495443 | 7/1992 | European Pat. Off. . |

(List continued on next page.)

OTHER PUBLICATIONS

Standard Urology Product Catalog, CIRCON ACMI: Stanford (1992).
Chang, Raymond J. et al, American Heart Journal, 125: 1276–1283 (May, 1993).
Cosman, Eric R. et al, Sterostatic and Functional Neurosurgery, pp. 2490–2499 (Date Unknown).
Diasonics, Brochure DIA 2000 171 CRF May 1988.
Perinchery, Narayan, "Neoplasms of the Prostate Gland."

(List continued on next page.)

*Primary Examiner*—C. Fred Rosenbaum
*Assistant Examiner*—Manuel Mendez
*Attorney, Agent, or Firm*—Flehr, Hohbach, Test, Albritton & Herbert

[57] ABSTRACT

A medical probe device including a catheter having a stylet guide housing with one or more stylet ports in a side wall thereof and guide means for directing a flexible stylet outward through the stylet port and through intervening tissue to a target tissue. The catheter assembly includes a stylet guide lumen communicating with the stylet port and a stylet positioned in said stylet guide lumen for longitudinal movement from the port through intervening tissue to a target tissue. The stylet can be an electrical conductor enclosed within a non-conductive layer, the electrical conductor being a radio frequency electrode. In normal action, the stylet and its surrounding sleeve are deployed out from the stylet port in the catheter into the desired target tissue. A sharpened tip on the stylet electrode facilitates the penetration of the intervening tissue, such as a urethra. If, however, the stylet is deployed into a dense or fibrous area of tissue or into an area of scar tissue in the urethra, the sharpened tip of the stylet might not immediately penetrate the urethra wall until sufficient pressure is applied to the stylet. By heating the stylet prior to extension of the stylet from the stylet port in the catheter, the passage of the stylet through the intervening tissue is facilitated. Once the stylet is in position in the target tissue, the normal operation of the stylet in emitting electromagnetic current for tissue ablation is commenced.

5 Claims, 8 Drawing Sheets

U.S. PATENT DOCUMENTS

| | | | |
|---|---|---|---|
| 2,047,535 | 7/1936 | Wappler . | |
| 2,118,631 | 5/1938 | Wappler . | |
| 2,710,000 | 6/1955 | Cromer et al. . | |
| 3,230,957 | 1/1966 | Seifert . | |
| 3,339,542 | 9/1967 | Howell . | |
| 3,556,079 | 1/1971 | Omizo et al. | 128/2 |
| 3,595,239 | 7/1971 | Petersen . | |
| 3,598,108 | 8/1971 | Jamshidi . | |
| 3,682,162 | 8/1972 | Colyer . | |
| 3,828,780 | 8/1974 | Morrison, Jr. . | |
| 3,835,842 | 9/1974 | Iglesias . | |
| 3,840,016 | 10/1974 | Lindemann . | |
| 3,850,175 | 11/1974 | Iglesias . | |
| 3,858,577 | 1/1975 | Bass et al. . | |
| 3,884,237 | 5/1975 | O'Malley et al. . | |
| 3,924,628 | 12/1975 | Droegemueller et al. . | |
| 3,939,840 | 2/1976 | Storz . | |
| 3,941,121 | 3/1976 | Olinger et al. . | |
| 3,942,530 | 3/1976 | Northeved . | |
| 3,948,270 | 4/1976 | Hasson . | |
| 3,991,770 | 11/1976 | Leveen . | |
| 4,011,872 | 3/1977 | Komiya . | |
| 4,119,102 | 10/1978 | Leveen . | |
| 4,121,592 | 10/1978 | Whalley . | |
| 4,136,566 | 1/1979 | Christensen . | |
| 4,137,920 | 2/1979 | Bonnet . | |
| 4,154,246 | 5/1979 | Leveen . | |
| 4,204,549 | 5/1980 | Paglione . | |
| 4,224,929 | 9/1980 | Furihata . | |
| 4,228,809 | 10/1980 | Paglione | 128/804 |
| 4,237,898 | 12/1980 | Whalley . | |
| 4,267,828 | 5/1981 | Matsuo . | |
| 4,295,467 | 10/1981 | Mann et al. . | |
| 4,307,720 | 12/1981 | Weber, Jr. . | |
| 4,311,145 | 1/1982 | Esty et al. . | |
| 4,311,154 | 1/1982 | Sterzer et al. . | |
| 4,312,364 | 1/1982 | Convert et al. . | |
| 4,336,809 | 6/1982 | Clark . | |
| 4,375,220 | 3/1983 | Matvias . | |
| 4,397,314 | 8/1983 | Vaguine . | |
| 4,402,311 | 9/1983 | Hattori . | |
| 4,405,314 | 9/1983 | Cope . | |
| 4,411,266 | 10/1983 | Cosman . | |
| 4,448,198 | 5/1984 | Turner . | |
| 4,452,236 | 6/1984 | Utsugi . | |
| 4,470,407 | 9/1984 | Hussein | 606/2 |
| 4,494,539 | 1/1985 | Zenitani et al. . | |
| 4,552,554 | 11/1985 | Gould et al. . | |
| 4,562,838 | 1/1986 | Walker . | |
| 4,565,200 | 1/1986 | Cosman . | |
| 4,568,329 | 2/1986 | Mahurkar . | |
| 4,580,551 | 4/1986 | Siegmund et al. . | |
| 4,594,074 | 6/1986 | Anderson et al. . | |
| 4,601,296 | 7/1986 | Yerushalmi . | |
| 4,612,940 | 9/1986 | Kasevich et al. . | |
| 4,658,836 | 4/1987 | Turner . | |
| 4,660,560 | 4/1987 | Klein . | |
| 4,669,475 | 6/1987 | Turner . | |
| 4,672,962 | 6/1987 | Hershenson . | |
| 4,676,258 | 6/1987 | Inokuchi et al. . | |
| 4,681,122 | 7/1987 | Winters et al. . | |
| 4,682,596 | 7/1987 | Bales et al. . | |
| 4,697,595 | 10/1987 | Breyer et al. . | |
| 4,700,716 | 10/1987 | Kasevich et al. . | |
| 4,706,681 | 11/1987 | Breyer et al. . | |
| 4,709,698 | 12/1987 | Johnston et al. . | |
| 4,719,914 | 1/1988 | Johnson . | |
| 4,753,223 | 6/1988 | Bremer . | |
| 4,765,331 | 8/1988 | Petruzzi et al. . | |
| 4,769,005 | 9/1988 | Ginsburg et al. . | |
| 4,774,949 | 10/1988 | Fogarty . | |
| 4,776,086 | 10/1988 | Kasevich et al. . | |
| 4,781,186 | 11/1988 | Simpson et al . | |
| 4,784,638 | 11/1988 | Ghajar et al. . | |
| 4,785,829 | 11/1988 | Convert et al. . | |
| 4,798,215 | 1/1989 | Turner . | |
| 4,800,899 | 1/1989 | Elliott . | |
| 4,805,616 | 2/1989 | Pao . | |
| 4,813,429 | 3/1989 | Eshel et al. . | |
| 4,817,601 | 4/1989 | Roth et al. . | |
| 4,818,954 | 4/1989 | Flachenecker et al. . | |
| 4,822,333 | 4/1989 | Lavarenne . | |
| 4,823,791 | 4/1989 | D'Amelio et al. . | |
| 4,823,812 | 4/1989 | Eshel et al. . | |
| 4,860,744 | 8/1989 | Johnson et al. . | |
| 4,865,047 | 9/1989 | Chou et al. . | |
| 4,872,458 | 10/1989 | Kanehira et al. . | |
| 4,887,615 | 12/1989 | Taylor . | |
| 4,893,623 | 1/1990 | Rosenbluth . | |
| 4,896,671 | 1/1990 | Cunningham et al. . | |
| 4,898,577 | 2/1990 | Badger . | |
| 4,905,667 | 3/1990 | Foerster et al. . | |
| 4,906,230 | 3/1990 | Maloney et al. . | |
| 4,907,758 | 3/1990 | Cosman . | |
| 4,911,148 | 5/1990 | Sosnowski et al. . | |
| 4,911,173 | 3/1990 | Terwilliger . | |
| 4,919,129 | 4/1990 | Weber, Jr. et al. . | |
| 4,920,978 | 5/1990 | Colvin . | |
| 4,932,958 | 6/1990 | Reddy et al. . | |
| 4,936,281 | 6/1990 | Stasz . | |
| 4,940,064 | 7/1990 | Desai . | |
| 4,943,290 | 7/1990 | Rexroth | 606/49 |
| 4,946,449 | 8/1990 | Davis, Jr. . | |
| 4,949,706 | 8/1990 | Thon . | |
| 4,950,267 | 8/1990 | Ishihara et al. | 606/12 |
| 4,955,377 | 9/1990 | Lennox et al. . | |
| 4,961,435 | 10/1990 | Kitagawa et al. . | |
| 4,966,597 | 10/1990 | Cosman . | |
| 4,967,765 | 11/1990 | Turner et al. . | |
| 4,982,724 | 1/1991 | Saito et al. . | |
| 4,994,062 | 2/1991 | Nishigaki et al. . | |
| 4,998,932 | 3/1991 | Rosen et al. . | |
| 4,998,933 | 3/1991 | Eggers et al. . | |
| 5,002,558 | 3/1991 | Klein et al. . | |
| 5,003,991 | 4/1991 | Takayama et al. . | |
| 5,007,437 | 4/1991 | Sterzer . | |
| 5,007,908 | 4/1991 | Rydell . | |
| 5,010,886 | 4/1991 | Passafaro et al. . | |
| 5,026,959 | 6/1991 | Ito et al. . | |
| 5,029,588 | 7/1991 | Yock et al. . | |
| 5,030,227 | 7/1991 | Rosenbluth et al. . | |
| 5,035,695 | 7/1991 | Weber, Jr. et al. . | |
| 5,035,696 | 7/1991 | Rydell . | |
| 5,045,056 | 9/1991 | Behl . | |
| 5,045,072 | 9/1991 | Castillo . | |
| 5,055,109 | 10/1991 | Gould et al. . | |
| 5,057,105 | 10/1991 | Malone et al. . | |
| 5,057,106 | 10/1991 | Kasevich et al. . | |
| 5,057,107 | 10/1991 | Parins . | |
| 5,059,851 | 10/1991 | Corl et al. . | |
| 5,060,660 | 10/1991 | Gambale et al. . | |
| 5,071,418 | 12/1991 | Rosenbaum | 606/45 |
| 5,080,660 | 1/1992 | Buelna . | |
| 5,083,565 | 1/1992 | Parins . | |
| 5,084,044 | 1/1992 | Quint . | |
| 5,100,423 | 3/1992 | Fearnot . | |
| 5,108,415 | 4/1992 | Pinchuk et al. . | |
| 5,109,859 | 5/1992 | Jenkins . | |
| 5,116,615 | 5/1992 | Gokcen et al. . | |
| 5,120,316 | 6/1992 | Morales et al. . | |
| 5,122,137 | 6/1992 | Lennox | 606/42 |
| 5,135,525 | 8/1992 | Biscoping et al. . | |

| | | |
|---|---|---|
| 5,150,717 | 9/1992 | Rosen et al. . |
| 5,170,787 | 12/1992 | Lindegren . |
| 5,178,620 | 1/1993 | Eggers et al. . |
| 5,179,962 | 1/1993 | Dutcher et al. . |
| 5,190,539 | 3/1993 | Fletcher et al. . |
| 5,195,965 | 3/1993 | Shantha . |
| 5,195,968 | 3/1993 | Lundquist et al. . |
| 5,197,963 | 3/1993 | Parins ........................................ 606/41 |
| 5,201,732 | 4/1993 | Parins et al. . |
| 5,207,672 | 5/1993 | Roth . |
| 5,220,927 | 6/1993 | Astrahan et al. . |
| 5,222,953 | 6/1993 | Dowlatshahi . |
| 5,228,441 | 7/1993 | Lundquist . |
| 5,234,004 | 8/1993 | Hascoet et al. .................... 607/102 |
| 5,235,964 | 8/1993 | Abenaim . |
| 5,249,585 | 10/1993 | Turner et al. ....................... 607/99 |
| 5,254,088 | 10/1993 | Lundquist et al. . |
| 5,257,451 | 11/1993 | Edwards et al. . |
| 5,273,524 | 12/1993 | Fox et al. . |
| 5,273,535 | 12/1993 | Edwards et al. . |
| 5,275,162 | 1/1994 | Edwards et al. . |
| 5,281,213 | 1/1994 | Milder et al. . |
| 5,281,217 | 1/1994 | Edwards et al. . |
| 5,281,218 | 1/1994 | Imran . |
| 5,287,845 | 2/1994 | Faul et al. . |
| 5,290,286 | 3/1994 | Parins . |
| 5,293,868 | 3/1994 | Nardella . |
| 5,293,869 | 3/1994 | Edwards et al. . |
| 5,299,559 | 4/1994 | Bruce et al. . |
| 5,300,068 | 4/1994 | Rosar et al. . |
| 5,300,069 | 4/1994 | Hunsberger et al. . |
| 5,300,070 | 4/1994 | Gentelia et al. . |
| 5,300,099 | 4/1994 | Rudie . |
| 5,301,687 | 4/1994 | Wong et al. . |
| 5,304,134 | 4/1994 | Kraus et al. . |
| 5,304,214 | 4/1994 | Deford . |
| 5,309,910 | 5/1994 | Edwards et al. . |
| 5,312,392 | 5/1994 | Hofstetter et al. . |
| 5,313,943 | 5/1994 | Houser et al. . |

FOREIGN PATENT DOCUMENTS

| | | |
|---|---|---|
| 521264A2 | 1/1993 | European Pat. Off. . |
| 2848484 | 5/1979 | Germany . |
| 2941060 | 4/1980 | Germany ............................. 604/48 |
| 3218314 | 6/1983 | Germany . |
| 3247793 | 7/1983 | Germany ............................. 604/48 |
| 3844131 | 12/1988 | Germany . |
| 3838840 | 5/1990 | Germany . |
| 2121675 | 5/1990 | Japan . |
| 9007303 | 7/1990 | WIPO . |
| WO911213 | 8/1991 | WIPO . |
| 9116859 | 11/1991 | WIPO . |
| 9207622 | 5/1992 | WIPO . |
| 9210142 | 6/1992 | WIPO . |
| WO92/10142 | 6/1992 | WIPO . |
| 9221285 | 12/1992 | WIPO . |
| 9221278 | 12/1992 | WIPO . |
| 9304727 | 4/1993 | WIPO . |
| 9308756 | 5/1993 | WIPO . |
| 9308755 | 5/1993 | WIPO . |
| 9320893 | 10/1993 | WIPO . |
| 9320886 | 10/1993 | WIPO . |
| 9320768 | 10/1993 | WIPO . |
| 9320767 | 10/1993 | WIPO . |
| 9308757 | 10/1993 | WIPO . |
| WO93/25136 | 12/1993 | WIPO . |
| 9403759 | 2/1994 | WIPO . |
| 9406377 | 3/1994 | WIPO . |
| 9405226 | 3/1994 | WIPO . |
| 9404222 | 3/1994 | WIPO . |
| 9407446 | 4/1994 | WIPO . |
| 9407549 | 4/1994 | WIPO . |
| 9407413 | 4/1994 | WIPO . |
| 9407412 | 4/1994 | WIPO . |
| 9407411 | 4/1994 | WIPO . |
| 9407441 | 4/1994 | WIPO . |
| 9407410 | 10/1994 | WIPO . |

OTHER PUBLICATIONS pp. 378–409 (Date Unknown).

Urology 5th ed., Storz, Jan. 1992.

Transuretheral μwave Thermotherapy for Prostatism: Early Mayo Foundation Experience: Blute, Mayo Clinic Proceedings: vol. 67 May 92, pp. 417–421.

New Therapies for Benign Prostatic Hyperplasia, Editorial Bruskewitz, Mayo Clinic Proceedings vol. 67 May 92 pp. 493–495.

Industry Strategies, Urology: "A Multi Billion Dollar Market . . . " Stephen Scala Nov. 19, 1991 pp. 1–32.

U.I. Dept. of Health and Human Services, MMWR 41: 401∝404 vol. 41, No. 23, (Jun. 12, 1992).

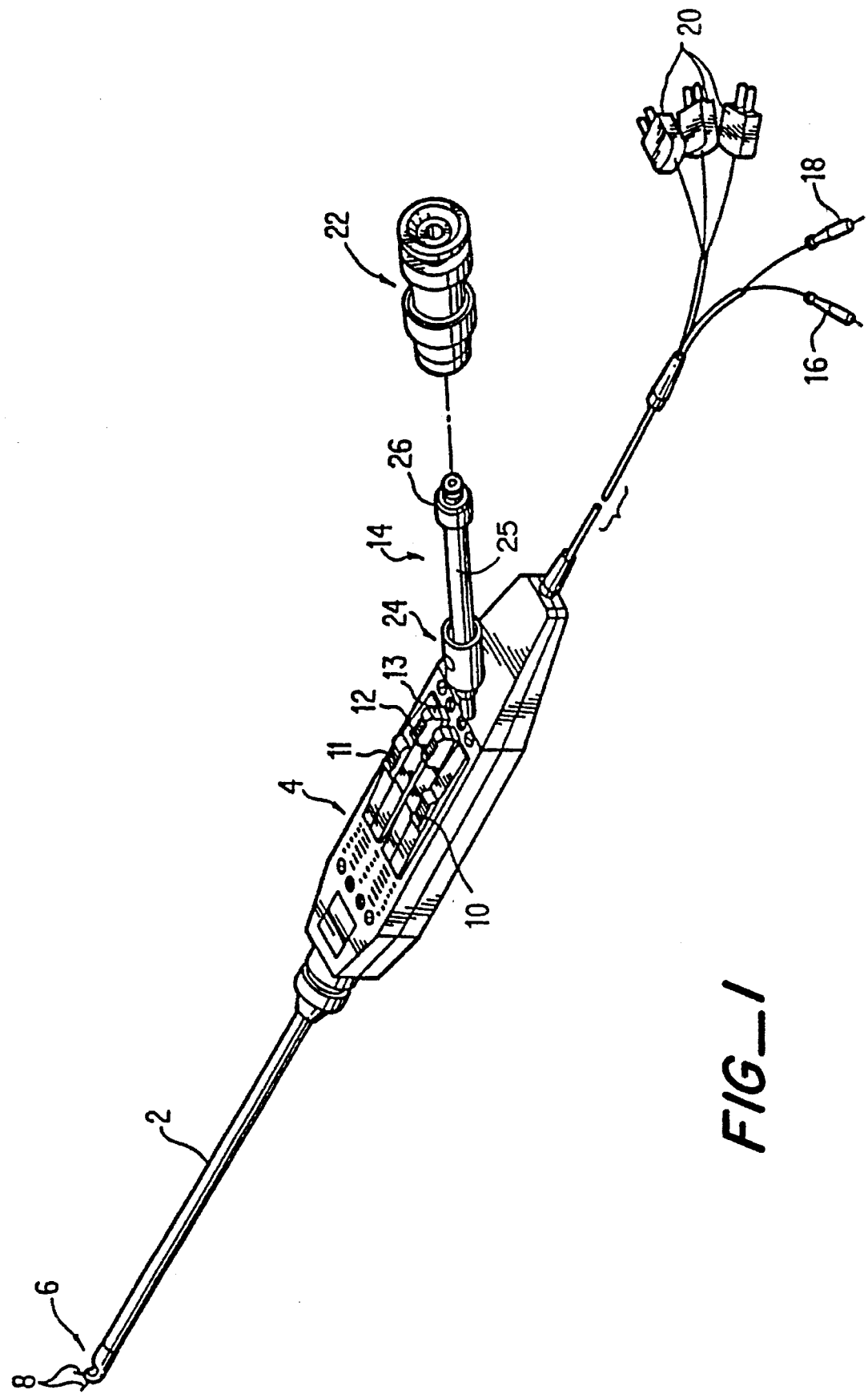
FIG_1

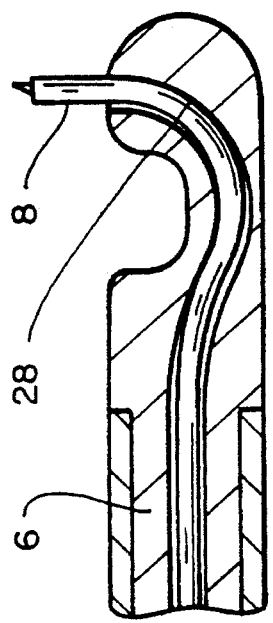
FIG_2
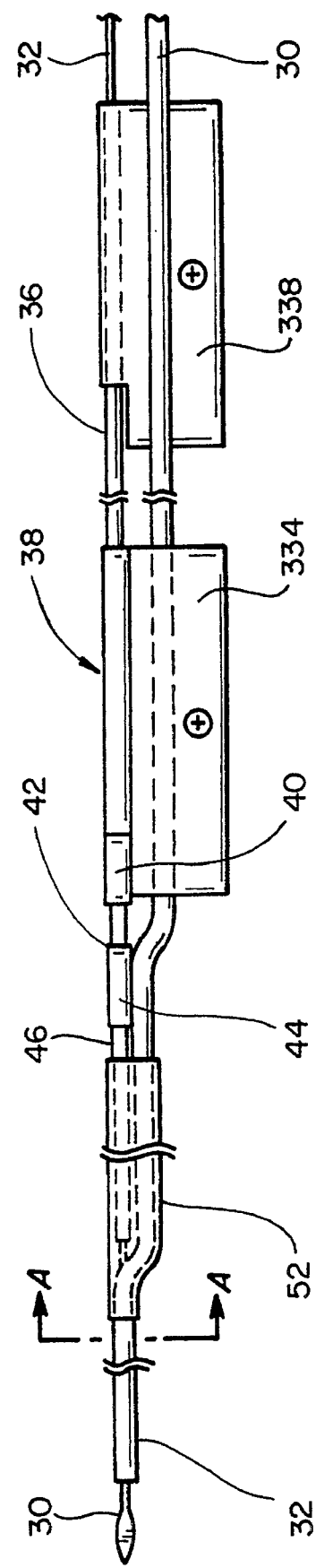
FIG_3

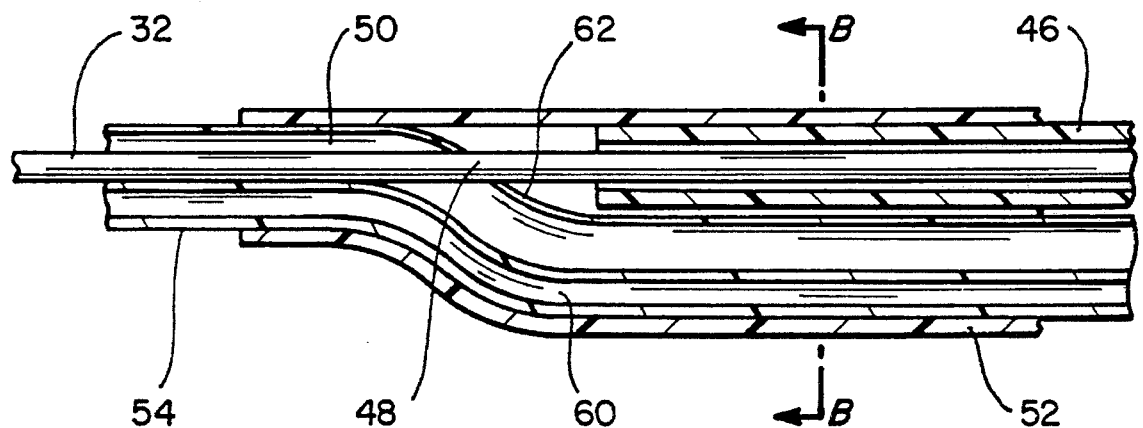
FIG_4
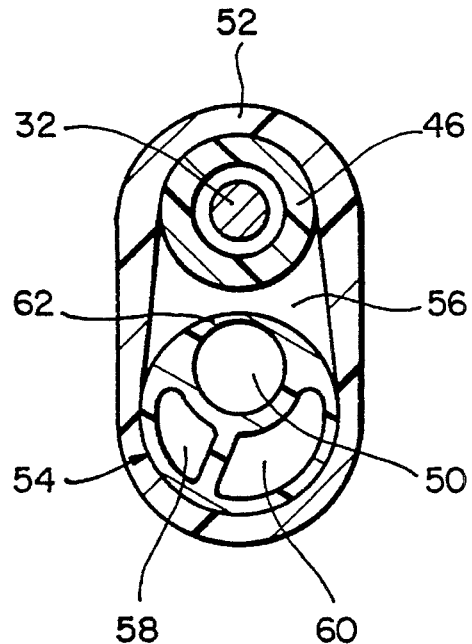
FIG_5

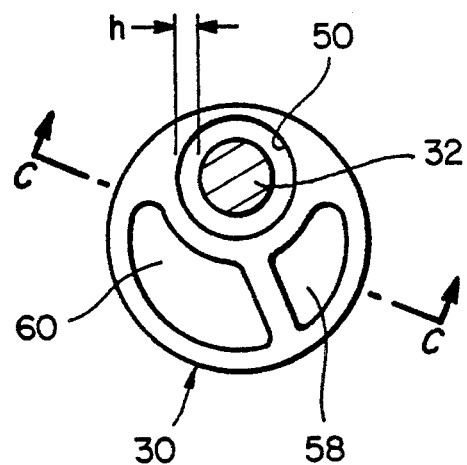
FIG_6
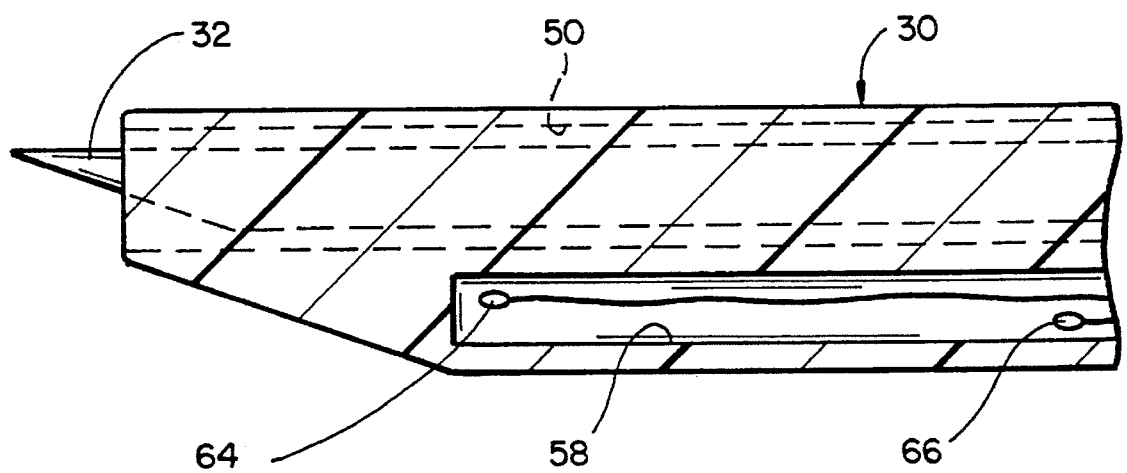
FIG_7

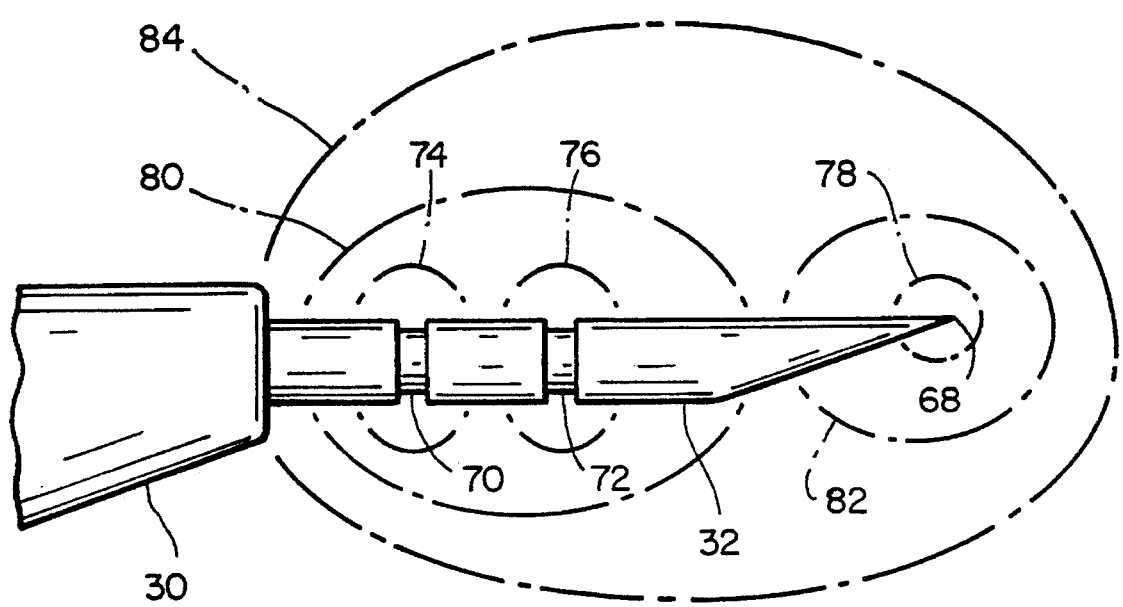
FIG_8
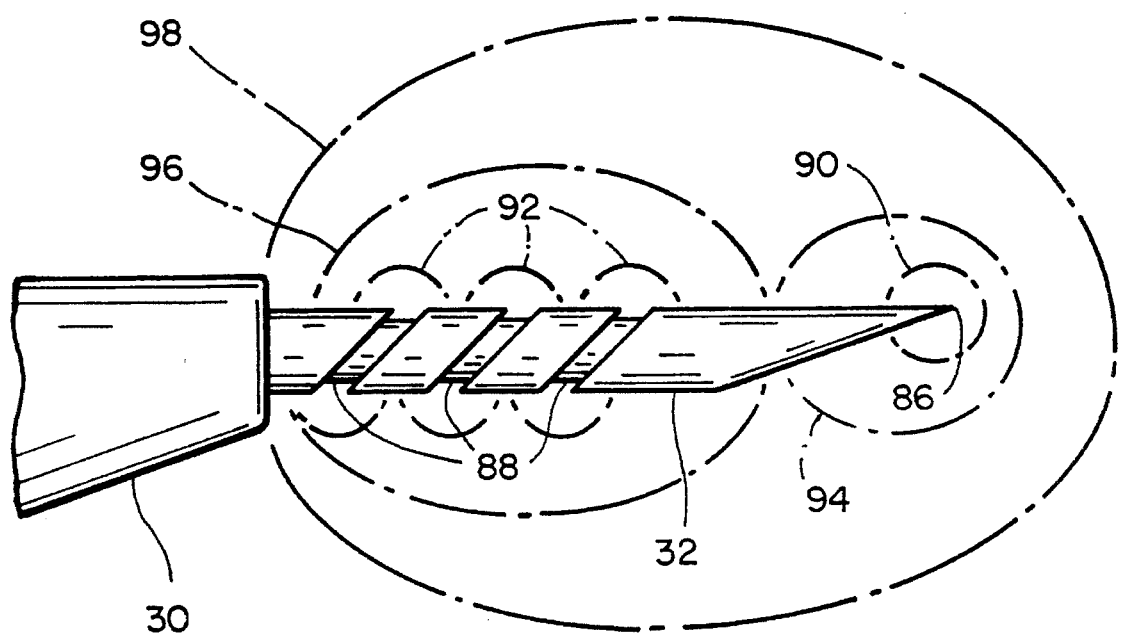
FIG_9

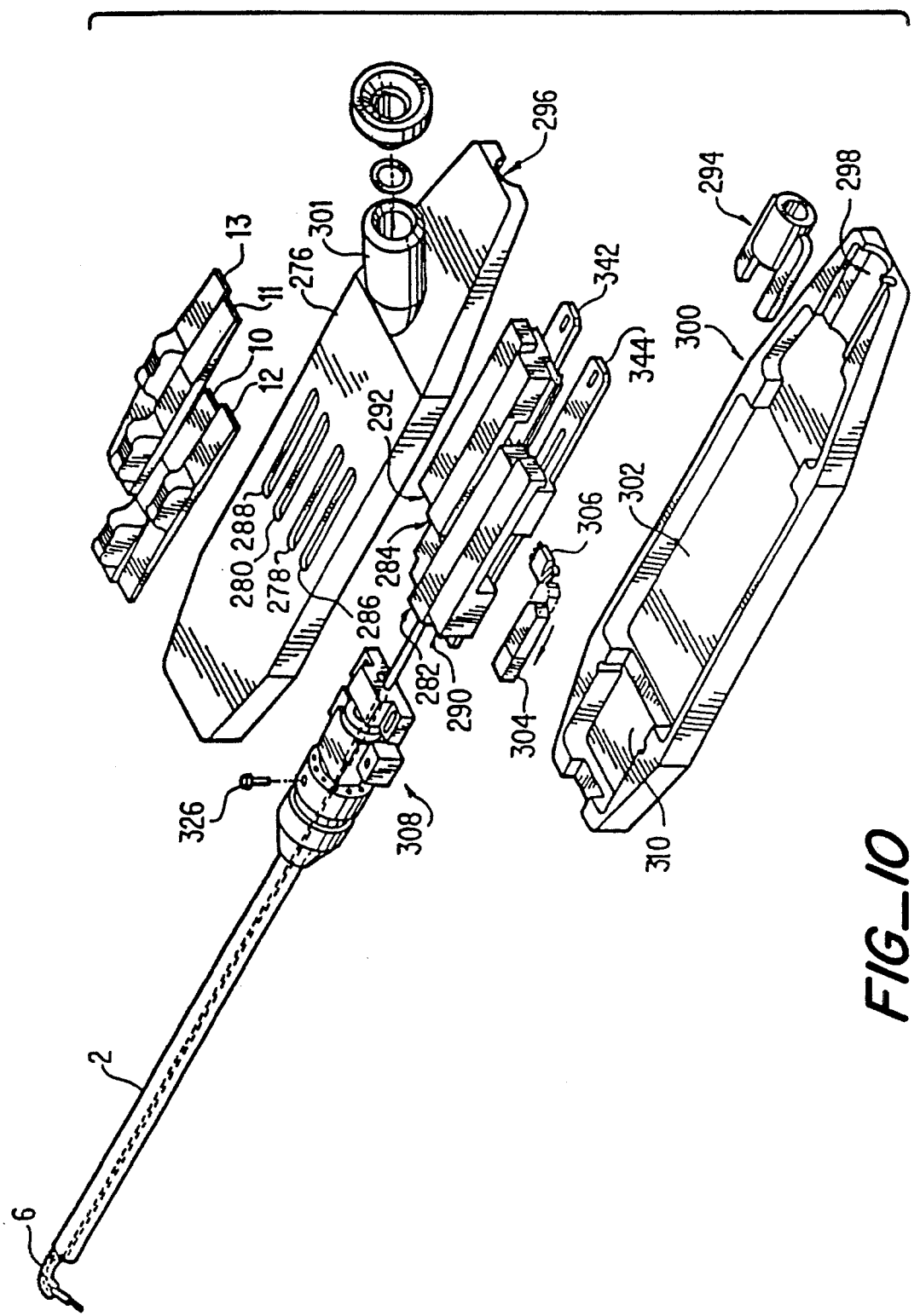
FIG_10

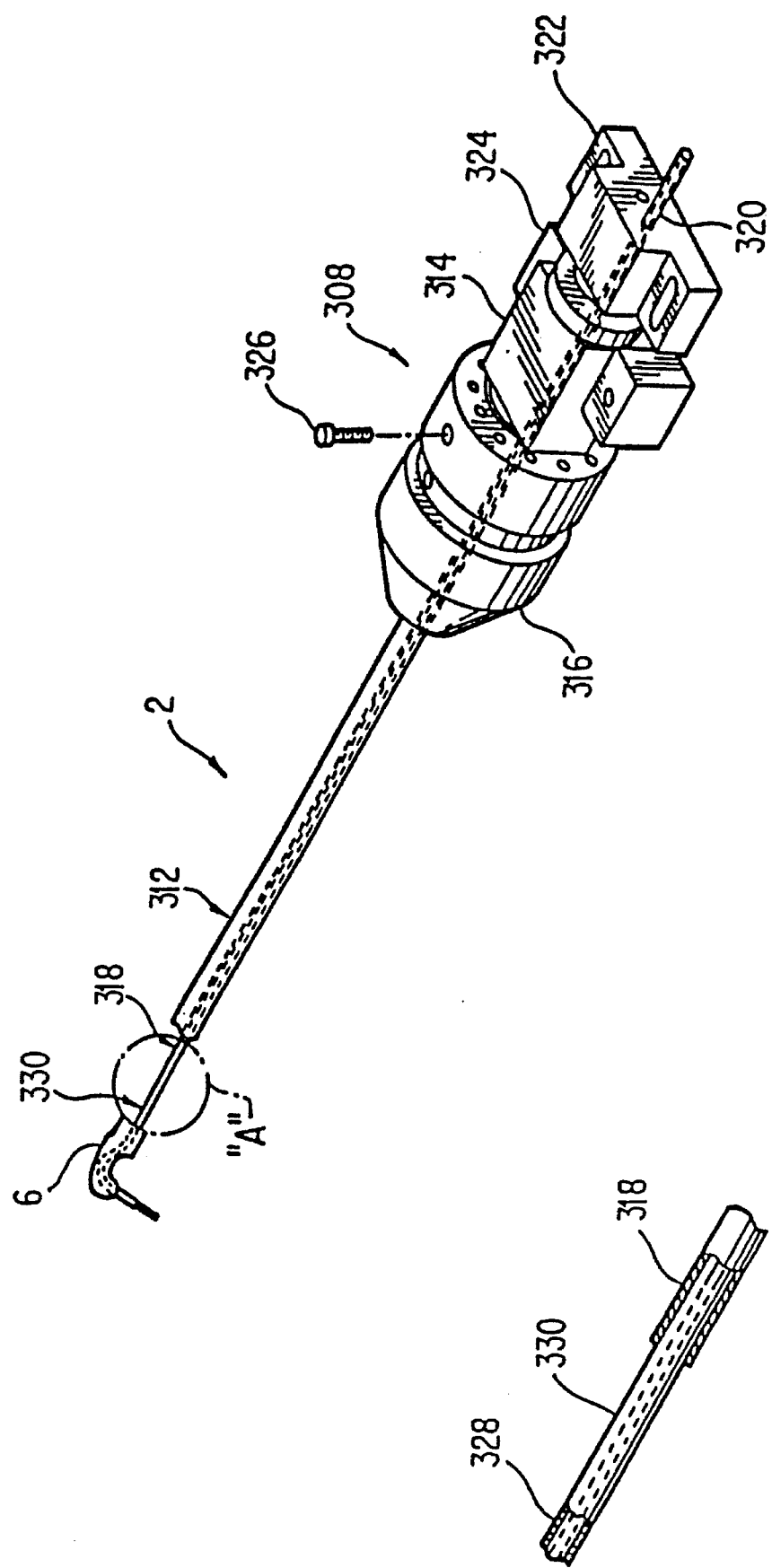
FIG_11
FIG_12

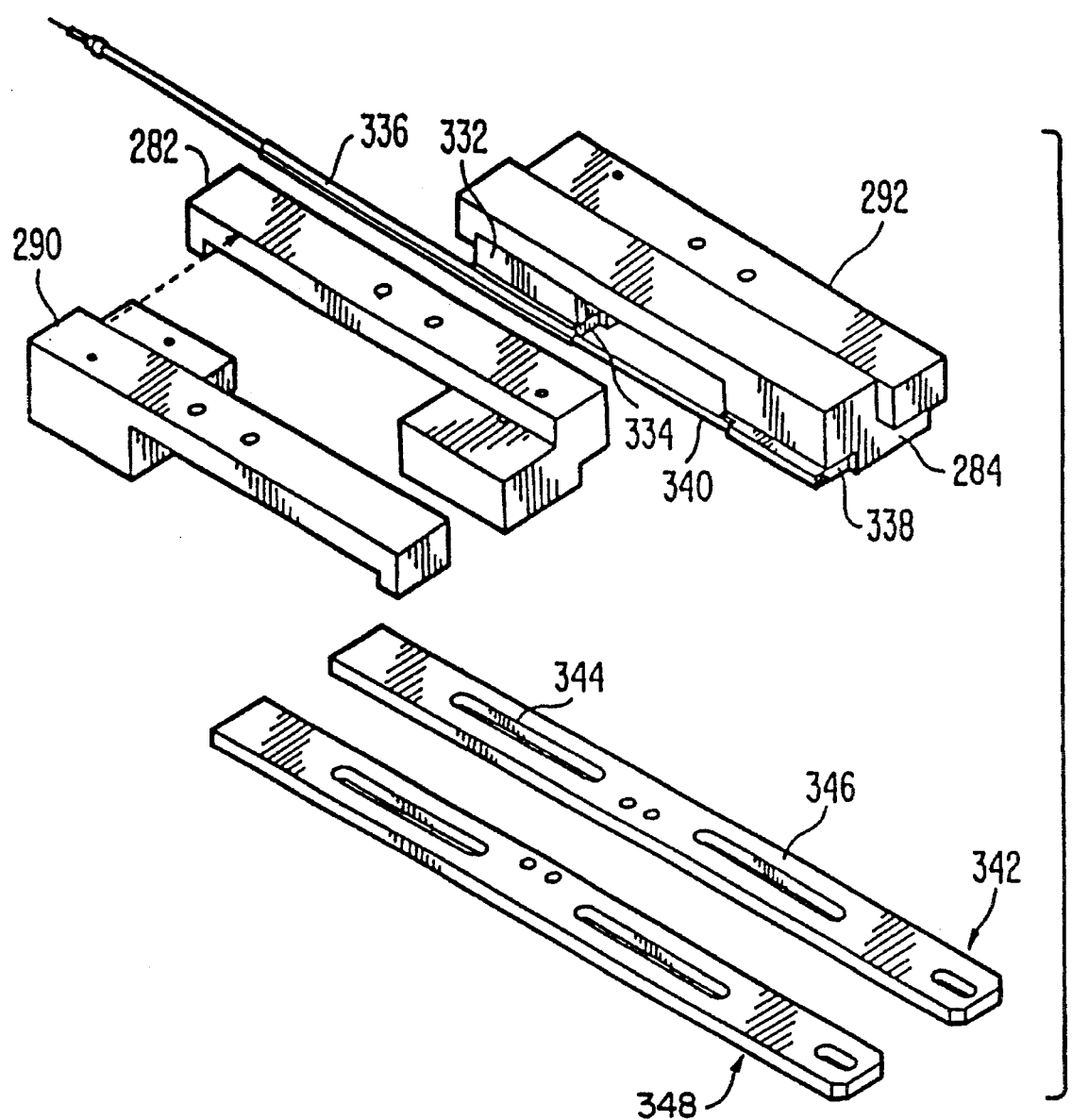
FIG_13

MEDICAL ABLATION APPARATUS UTILIZING A HEATED STYLET

RELATIONSHIP TO COPENDING APPLICATION

This application is a continuation-in-part of applications Ser. No. 07/929,638 filed Aug. 12, 1992, now abandoned; Ser. No. 08/012,370 filed Feb. 2, 1993, and now U.S. Pat. No. 5,370,675; Ser. No. 08/062,364 filed May 13, 1993 and still pending; and Ser. No. 08/061,647 filed May 13, 1993, and now U.S. Pat. No. 5,421,819. The entire contents of all of the above applications are hereby incorporated by reference.

FIELD OF THE INVENTION

This invention is directed to a unique device and method for penetrating body tissues for medical purposes such as tissue ablation and fluid substance delivery, for example. The device penetrates tissue to the precise target selected in order to deliver energy to the tissue and/or deliver substances. It limits this treatment to the precise preselected site, thereby minimizing trauma to normal surrounding tissue and achieving a greater medical benefit. This device is a catheter-like device for positioning a treatment assembly in the area or organ selected for medical treatment with one or more stylets in the catheter, mounted for extension from a stylet port in the side of the catheter through surrounding tissue to the tissue targeted for medical intervention.

Specifically, this invention, relates to a method and apparatus for deploying an operating stylet into target tissue via intervening tissue by heating the stylet prior to extension of the stylet from the stylet port in the catheter. Once the stylet is in position, the normal operation of the stylet in emitting electromagnetic current is commenced.

BACKGROUND OF THE INVENTION

Treatment of cellular tissues usually requires direct contact of target tissue with a medical instrument, usually by surgical procedures exposing both the target and intervening tissue to substantial trauma. Often, precise placement of a treatment probe is difficult because of the location of targeted tissues in the body or the proximity of the target tissue to easily damaged, critical body organs, nerves, or other components.

Benign prostatic hypertrophy or hyperplasia (BPH), for example, is one of the most common medical problems experienced by men over 50 years old. Urinary tract obstruction due to prostatic hyperplasia has been recognized since the earliest days of medicine. Hyperplastic enlargement of the prostate gland often leads to compression of the urethra, resulting in obstruction of the urinary tract and the subsequent development of symptoms including frequent urination, decrease in urinary flow, nocturia, pain, discomfort, and dribbling. The association of BPH with aging has been shown to exceed 50% in men over 50 years of age and increases in incidence to over 75% in men over 80 years of age. Symptoms of urinary obstruction occur most frequently between the ages of 65 and 70 when approximately 65% of men in this age group have prostatic enlargement.

Currently there is no proven effective nonsurgical method of treatment of BPH. In addition, the surgical procedures available are not totally satisfactory. Currently patients suffering from the obstructive symptoms of this disease are provided with few options: continue to cope with the symptoms (i.e., conservative management), submit to drug therapy at early stages, or submit to surgical intervention. More than 430,000 patients per year undergo surgery for removal of prostatic tissue in the United States. These represent less than five percent of men exhibiting clinical significant symptoms.

Those suffering from BPH are often elderly men, many with additional health problems which increase the risk of surgical procedures. Surgical procedures for the removal of prostatic tissue are associated with a number of hazards including anesthesia related morbidity, hemorrhage, coagulopathies, pulmonary emboli, and electrolyte imbalances. These procedures performed currently can also lead to cardiac complications, bladder perforation, incontinence, infection, urethral or bladder neck stricture, retention of prostatic chips, retrograde ejaculation, and infertility. Due to the extensive invasive nature of the current treatment options for obstructive uropathy, the majority of patients delay definitive treatment of their condition. This circumstance can lead to serious damage to structures secondary to the obstructive lesion in the prostate (bladder hypertrophy, hydronephrosis, dilation of the kidney pelvis, chronic infection, dilation of ureters, etc.) which is not without significant consequences. In addition, a significant number of patients with symptoms sufficiently severe to warrant surgical intervention are therefore poor operative risks and are poor candidates for prostatectomy. In addition, younger men suffering from BPH who do not desire to risk complications such as infertility are often forced to avoid surgical intervention. Thus the need, importance and value of improved surgical and non-surgical methods for treating BPH is unquestionable.

High-frequency currents are used in electrocautery procedures for cutting human tissue especially when a bloodless incision is desired or when the operating site is not accessible with a normal scalpel but presents an access for a thin instrument through natural body openings such as the esophagus, intestines or urethra. Examples include the removal of prostatic adenomas, bladder tumors or intestinal polyps. In such cases, the high-frequency current is fed by a surgical probe into the tissue to be cut. The resulting dissipated heat causes boiling and vaporization of the cell fluid at this point, whereupon the cell walls rupture and the tissue is separated.

Destruction of cellular tissues in situ has been used in the treatment of many diseases and medical conditions alone or as an adjunct to surgical removal procedures. It is often less traumatic than surgical procedures and may be the only alternative where other procedures are unsafe. Ablative treatment devices have the advantage of using an electromagnetic energy which is rapidly dissipated and reduced to a non-destructive level by conduction and convection forces of circulating fluids and other natural body processes.

Microwave, radio frequency, acoustical (ultrasound) and light energy (laser) devices, and tissue destructive substances have been used to destroy malignant, benign and other types of cells and tissues from a wide variety of anatomic sites and organs. Tissues treated include isolated carcinoma masses and, more specifically, organs such as the prostate, glandular and stromal nodules characteristic of benign prostate hyperplasia. These devices typically include a catheter or cannula which is used to carry a radio frequency electrode or microwave antenna through a duct to the zone of treatment and apply energy diffusely through the duct wall into the surrounding tissue in all directions. Severe trauma is often sustained by the duct wall during this cellular destruction process, and some devices combine cooling systems with microwave antennas to reduce trauma to the ductal wall. For treating the prostate with these devices, for example, heat energy is delivered through the walls of the urethra into the surrounding prostate cells in an effort to ablate the tissue causing the constriction of the urethra. Light energy, typically from a laser, is delivered to prostate tissue target sites by "burning through" the wall of the urethra. Healthy cells of the duct wall and healthy tissue between the, nodules and duct wall are also indiscriminately destroyed in the process and can cause unnecessary loss of some prostate function. Furthermore, the added cooling function of some microwave devices complicates the apparatus and requires that the device be sufficiently large to accommodate this cooling system.

Application of liquids to specific tissues for medical purposes is limited by the ability to obtain delivery without traumatizing intervening tissue and to effect a delivery limited to the specific target tissue. Localized chemotherapy, drug infusions, collagen injections, or injections of agents which are then activated by light, heat or chemicals would be greatly facilitated by a device which could conveniently and precisely place a fluid (liquid or gas) supply catheter opening at the specific target tissue.

The previously filed patent applications cited above, hereby incorporated by reference, disclose a medical probe device which comprises a catheter having a stylet guide housing with at least one stylet port in a side thereof and stylet guide apparatus for directing a flexible stylet outward through at least one stylet port and through intervening tissue to targeted tissues. The stylet guide housing has an optical viewer positioned for viewing the stylet which includes a fiber optic channel for receiving a fiber optic viewing device. The device preferably includes a flushing liquid channel in the stylet guide housing having an exit port positioned to direct flushing liquid issuing therefrom across the end of the fiber optic device when positioned in the viewing zone. The stylet comprises an electrical conductor enclosed within a non-conductive sleeve, the electrical conductor being a radio frequency electrode.

In normal action, the stylet and its surrounding sleeve are deployed out from the stylet port in the catheter into the desired target tissue. A sharpened tip on the; stylet electrode facilitates the penetration of the intervening tissue, such as a urethra. If, however, the stylet is deployed into a dense or fibrous area of tissue or into an area of scar tissue in the urethra, the sharpened tip of the stylet might not immediately penetrate the urethra wall until sufficient pressure is applied the stylet. It was found that, in certain places of dense tissue, the urethra wall can be distended almost 1 cm before the stylet punctures the urethra wall.

OBJECTS AND SUMMARY OF THE INVENTION

It is an object of this invention to provide a device and method for penetrating tissue, through intervening tissues to the precise target tissue selected for a medical action such as tissue ablation and/or substance delivery, limiting this activity to the precise preselected site, thereby minimizing the trauma and achieving a greater medical benefit.

It is an object of this invention to provide a device and method to allow easier penetration of intervening or other tissue by a sharpened stylet by heating said stylet prior to deployment into intervening tissue.

It is another object of the present invention to heat a stylet electrode to aid the stylet being inserted into intervening tissue, by making the tissue more plastic and pliable, and subsequently into target tissue.

It is another object of this invention to provide a stylet arrangement for penetration of intervening tissue to target tissue with a first temperature range for insertion of said stylet in the intervening tissue, and a second temperature range for medical treatment of the target tissue.

In summary, the method of medical treatment of this invention includes the following steps. Introducing a catheter to a zone adjacent to said tissue mass to be treated. Moving a flexible stylet from the catheter through a catheter port in the sidewall of the catheter and through surrounding tissue into said target tissue to be treated, said stylet being a conductive electrode. Heating said stylet to a predetermined temperature by applying RF energy at a first level high enough to heat body tissue to facilitate the passage of said stylet through said surrounding tissue. Further applying RF energy to said stylet at a second level high enough to apply RF current to said target tissue, said second level being high enough to kill living tissue but not high enough to immediately destroy said tissue.

Further, this invention also includes these steps. Advancing an electrical conductor to surrounding tissue adjacent to said target tissue to be ablated, the conductor being a flexible stylet surrounded by a movable non-conductive sleeve. Moving the non-conductive sleeve to remove it from a first position on said conductor to a second position on said conductor positioned at said surrounding tissue. Generating heat in said electrical conductor from an electric current in said conductor sufficient to soften and make pliable contiguous tissue to facilitate the passage of said conductor through said surrounding tissue to said target tissue. Moving said electrical conductor through said surrounding tissue into said target tissue. Further generating heat at a lower level by an electrical current in said electrode through said target tissue sufficient to kill said target tissue but insufficient to destroy said target tissue.

Also included are the following steps. Introducing a catheter to a zone adjacent to said tissue mass to be treated. Moving a flexible stylet from the catheter through a catheter port in the sidewall of the catheter and through surrounding tissue into said target tissue to be treated, said stylet being a conductive electrode. Heating said stylet to a first temperature range by applying RF energy at a first level to facilitate the passage of said stylet through said surrounding tissue. Further heating said stylet to a second temperature range by further applying RF energy to said stylet at a second level to provide a medical treatment to said target tissue. The first heating step comprises applying heat to said stylet to soften and make more plastic contiguous tissue, and wherein said second heating step comprises applying heat at a lower level sufficient only to kill said target tissue

BRIEF DESCRIPTION OF THE DRAWINGS

FIG. 1 is an isometric view of an RF ablation catheter embodiment of this invention with an fiber optic viewing accessory.

FIG. 2 is a cross-sectional view of a catheter of FIG. 1 showing details of the stylet guide housing.

FIG. 3 is a side view of the stylet and lumen assembly of this invention.

FIG. 4 is a cross-sectional side view of the of the junction of the stylet and control tube assembly taken along the central axis of the tubing.

FIG. 5 is a cross-sectional view of the junction of the stylet and control tube assembly taken along the line B—B of FIG. 4.

FIG. 6 is a cross-sectional view of a trilumen stylet of this invention taken along the line A—A in FIG. 3.

FIG. 7 is a cross-sectional side view of the trilumen stylet tip shown in FIG. 3 taken along line C—C of FIG. 6.

FIG. 8 is a plane view of the annular groove embodiment of the current density focusing electrode of this invention.

FIG. 9 is a plane view of the spiral groove embodiment of the current density focusing electrode of this invention.

FIG. 10 is an exploded view of the RF ablation catheter shown in FIG. 1.

FIG. 11 is an isometric view of the adjuster block and tension tube assembly of the RF ablation catheter shown in FIG. 10.

FIG. 12 is a detailed view "A" of the tension tube connections shown in FIG. 11.

FIG. 13 is an exploded view of the sleeve and electrode slide block assembly of the embodiment shown in FIG. 10.

DETAILED DESCRIPTION OF THE INVENTION

The device of this invention provides a precise controlled positioning of a treatment stylet in a tissue targeted for treatment, destruction or sampling from a catheter positioned in the vicinity of the target tissue.

The term "stylet" as used herein is defined to include both solid and hollow probes which are desired to be passed from a catheter port through normal tissue to targeted tissues. The stylet is shaped to facilitate easy passage through tissue. It can be a solid wire, thin rod, or other solid shape or it can be a thin hollow tube or other shape having a longitudinal lumen for introducing fluids to or removing materials from a site. The stylet can also be a thin hollow tube or other hollow shape, the hollow lumen thereof containing a reinforcing or functional rod or tube such as a laser fiber optic. The stylet preferably has a sharpened end to reduce resistance and trauma when it is pushed through tissue to a target site.

The stylet can be designed to provide a variety of medically desired treatments of a selected tissue. As a radio frequency electrode or microwave antenna, it can be used to ablate or destroy targeted tissues. As a hollow tube, it can be used to deliver a treatment fluid such as a liquid to targeted tissues. The liquid can be a simple solution or a suspension of solids, for example, colloidal particles, in a liquid. Since the stylet is very thin, it can be directed from the catheter through intervening normal tissue with a minimum of trauma to the normal tissue.

The device and method of this invention provide a more precise, controlled medical treatment which is suitable for destroying cells of medically targeted tissues throughout the body, both within and external to body organs. The device and method are particularly useful for treating benign prostate hyperplasia (BPH), and the device and its use are hereinafter described with respect to BPH, for purposes of simplifying the description thereof. It will be readily apparent to a person skilled in the art that the device and method can be used to destroy body tissues in any body cavities or tissue locations that are accessible by percutaneous or endoscopic catheters, and is not limited to the prostate. Application of the device and method in all of these organs and tissues are intended to be included within the scope of this invention.

BPH is a condition which arises from the replication and growth of cells in the prostate and the decrease of cell death rate, forming glandular and stromal nodules which expand the prostate and constrict the opening of the prostatic urethra. Glandular nodules are primarily concentrated within the transition zone, and stromal nodules within the periurethral region. Traditional treatments of this condition have included surgical removal of the entire prostate gland, digital removal of the adenoma, as well as transurethral resection of the urethral canal and prostate to remove tissue and widen the passageway. One significant and serious complication associated with these procedures is iatrogenic sterility. More recently, laser treatment has been employed to remove tissue, limiting bleeding and loss of body fluids. Balloons have also been expanded within the urethra to enlarge its diameter, with and without heat, but have been found to have significant limitations.

Microwave therapy has been utilized with some success by positioning a microwave antenna within the prostatic urethra and generating heat in the tissue surrounding the urethra with an electromagnetic field. Coolants are sometimes applied within the catheter shaft to reduce the temperature of the urethral wall. This necessitates complicated mechanisms to provide both cooling of the immediately adjacent tissues while generating heat in the more distant prostatic tissue. This technique is similar to microwave hyperthermia. Similarly, radio frequency tissue ablation with electrodes positioned within the urethra exposes the urethral wall to destructive temperatures. To avoid this, low temperature settings required to protect the urethra must be so low that the treatment time required to produce any useful effect is unduly extended, e.g. up to three hours of energy application.

One embodiment of the device of this invention uses the urethra to access the prostate and positions RF electrode stylets directly into the tissues to be destroyed. The portion of the stylet conductor extending from the urethra and into targeted tissues is usually enclosed within a longitudinally adjustable sleeve shield which prevents exposure of the tissue adjacent to the sleeve to the RF current. The sleeve movement is also used to control the amount of energy per unit surface area which is delivered by controlling the amount of electrode exposed. However, in this invention where there is anticipated a more dense intervening tissue obstruction or there is viewed a distending of the intervening tissue without penetration of the intervening tissue by a sharpened stylet, the insulating sleeve can be retracted prior to penetration through the intervening tissue, such as a urethra. Then the exposed electrode can by applied with a short duration of RF current sufficient to cause heating of the electrode and destruction of the tissue as the stylet electrode is introduced into the intervening tissue. Other aspects of the invention will become apparent from the drawings and accompanying descriptions of the device and method of this invention. It will be readily apparent to a person skilled in the art that this procedure can be used in many areas of the body for percutaneous approaches and approaches through body orifices.

FIG. 1 is an isometric view of an RF ablation catheter embodiment of this invention with a fiber optic viewing accessory. The flexible catheter 2, attached to handle 4, has a terminal stylet guide 6 with two stylets 8. The handle has stylet sleeve tabs 10 and 11 and electrode tabs 12 and 13 as will be described in greater detail hereinafter. The handle 4 is also connected to a optical viewing assembly 14 and RF power connector 16, transponder connector 18 and thermocouple connectors 20. The portions of the catheter 2 leading from the handle 4 to the stylet guide tip 6 can optionally have a graduated stiffness. For example, the catheter can be designed to be more stiff near the handle and more flexible near the tip, or any other stiffness profiles. The catheter can be constructed of an inner slotted stainless steel tube with outer flexible sleeve such as is described in copending application Ser. No. 790,648 filed Aug. 11, 1991 (corresponding to published Australian patent application Ser. No. 9210858), the entire contents of which are incorporated herein by reference. It can also be made of coiled or braided wire to which an outer sleeve is bonded.

The fiber optic viewing assembly in this embodiment includes a lens focusing assembly 22, a lens viewing assembly support connector 24 assembly attached to a male quick disconnect connector 26 by flexible tubing 28.

FIG. 2 is a cross-sectional view of a catheter of FIG. 1 showing details of the stylet guide housing. The stylet guide housing 6 has a curved passageway 28 through which the stylet 8 is extended into the tissue to be treated. Further details of these components are described in copending applications Ser. No. 08/01 2,370 filed Feb. 2, 1993, and application Ser. No. 08/062,647 filed May 13, 1993.

FIG. 3 is a side view of the stylet and lumen assembly of this invention. The key components of the stylet of this embodiment are an insulating sleeve 30 and an electrode 32 extending therethrough. The electrode 32 has a sharpened tip, in this embodiment a broadened spear tip. The proximal end of the electrode and sleeve are connected by respective sleeve connector 334 and electrode connector 336 to handle sleeve and electrode slides described in greater detail hereinafter with respect to FIGS. 10 and 13. An electrode support tube 36 extends from the electrode connector 336 to the area 38 of the sleeve connector 334 to transmit compressive pressure without collapsing the electrode 32. An insulating sleeve support tube 40 made of shrink tubing extends from the sleeve connector 334 to the beginning or proximal end 42 of the outer tubing 44. Tubing 44 joins the support tubing to the control tube 46. The control tube 46 supporting both the electrode and insulating sleeve extends to the junction 48 (see FIG. 4) of the electrode lumen passageway 50 and the electrode 32. In this manner, support is provided over the length of the stylet extending from the handle to the trilumen tip, preventing collapse or loss of linearity of the highly flexible electrode when it is pushed through the stylet guide housing.

FIG. 4 is a cross-sectional side view of the of the junction of the stylet and control tube assembly taken along the central axis of the tubing, and FIG. 5 is a cross-sectional view of the junction of the stylet and control tube assembly taken along the line B—B of FIG. 4. At the junction 48, the electrode 32 extends through the upper electrode lumen wall 62 and enters the electrode lumen 50. The outer tubing 52 encloses and supports both the distal ends of the control tubing 46 and trilumen sleeve tube 54.

Referring to FIG. 5, the space 56 between the control tube 46 and the trilumen 56 can be filled with adhesive to secure them together. The trilumen includes an electrode lumen 50, a temperature sensor lumen 58 and a fluid supply lumen 60 for supply of optional fluids such as antibiotics or anesthetics to the area of treatment.

FIG. 6 is a cross-sectional view of a trilumen stylet of this invention taken along the line A—A in FIG. 3. The trilumen sleeve 30 is an insulating sleeve for the electrode 32 and includes the additional temperature sensor lumen 58 and liquid supply lumen 60. The inner surface of the electrode lumina can be spaced from the outer surface of the electrode by a distance "h" which can be, for example, from about 1 to 3 mm to define an additional liquid supply conduit with an approximate annular cross-section.

FIG. 7 is a cross-sectional side view of the trilumen stylet tip shown in FIG. 6 taken along the line C—C. The terminal end of the temperature sensor lumen 58 is sealed to protect the electrical components. Thermocouple 64 is placed at the distal end of the sleeve 30 to monitor the temperature of the tissue surrounding the electrode 32 and is preferably less than about 1 mm from the exposed electrode. Thermocouple 66 is placed at least 3 mm and preferably from about 3 to 6 mm from the tip of sleeve 30 to monitor the temperature of the duct wall (such as the urethra) through which the stylet is extended. This is provided to insure the duct wall temperature does not reach destructive levels when the RF treatment of tissue surrounding the extended electrode is underway.

FIG. 8 is a plane view of the annular groove embodiment of the current density focusing electrode of this invention. In this embodiment, the electrode is ground to a single current focusing sharp tip 68 without secondary corner or other sharp edges which could also focus or crowd current. Additional current focusing can be provided along the electrode surface by the annular grooves 70 and 72. The temperature of the tissue surrounding the electrode initially increase in initial zones 74, 76 and 78. The elevated temperature zone then extends to two intermediate zones 80 and 82, as the zones from the grooves merge. Thereafter all of the elevated temperature zones merge to form the single oval zone lesion 84. Use of these current focusing grooves 70 and 72 produces a more symmetrical lesion.

FIG. 9 is a plane view of the spiral groove embodiment of the current density focusing electrode of this invention. In this embodiment, the electrode is also ground to a single current focusing sharp tip 86 without secondary sharp corners or edges which could also focus or crowd current. Additional current focusing can be provided along the electrode surface by at least one spiral or helical groove 88. The temperature of the tissue surrounding the electrode initially increase in the initial tip zone 90 and a spiral zone 92. The elevated temperature zone then extends to two intermediate zones 94 and 96, as the spiral zone 92 merges to form a single zone 96. Thereafter, all of the elevated temperature zones merge to form the single oval zone lesion 98. Use of the spiral focusing groove 88 provides a more symmetrical lesion.

FIG. 10 is an exploded view of the RF ablation catheter assembly shown in FIG. 1. The upper handle plate 276 has two central slots 278 and 280 through which the electrode control slides 10 are attached to respective left electrode slide block 282 and right electrode slide block 284. Sleeve control slides 12 are attached through outer slots 286 and 288 to respective left sleeve slide block 290 and right sleeve slide block 292. Fiber optic receptor housing 30 is mounted on the proximal surface of the upper handle plate 276. The electrical receptor 294 is received in respective cavities 296 and 298 in the upper handle plate 276 and lower handle plate 300 attached thereto. The lower handle plate 300 has a central cavity 302 which accommodates the electrode and sleeve slide blocks and associated elements.

Microswitch activator blocks 304 (only left sleeve block shown) are connected to the sleeve slide blocks 290 and 292. They are positioned to actuate the microswitches 306 when the respective sleeve block (and sleeve attached thereto) have been advanced. The microswitches 306 hold the respective RF power circuits open until the respective sleeves are advanced to a position beyond the urethra wall and into the prostate to prevent direct exposure of the urethra to the energized RF electrodes. Extension of the sleeve 5 mm beyond the guide is usually sufficient to protect the urethra.

The tension-torque tube assembly 308 is mounted in the distal end of the housing in the receptor 310.

FIG. 11 is an isometric view of the adjuster block and tension tube assembly 308 of the RF ablation catheter shown in FIG. 10. The torque tube 312 extends from the torque coupler 314 through the twist control knob 316 to the stylet guide 6. Bending flexure of the torque tube 312 during use lengthens the path from the handle to the guide tip 6. To prevent a resulting retraction of the stylet sleeve and electrode components when the torque tube 312 is flexed, a tension tube 318 having a fixed length and diameter smaller than the inner diameter of the torque tube 312 is provided. The distal end of the tension tube 318 is securely attached to the stylet guide 6, and the proximal end 320 is secured to the adjuster block 322, for example, by an adhesive. The axial position of the adjuster block 322 can be adjusted to insure the stylets are initially positioned just inside the outlet ports in the stylet guide 6. Torque coupler 31 4 is mounted on the coupler block 324. Twist control knob stop pin 326 extends into a groove (not shown) and limits rotation of the control knob 316.

FIG. 12 is a detailed view "A" of the distal end tension tube connections of the tension tube shown in FIG. 11. The tension tube 318 is securely connected to the proximal end 328 of the stylet guide 6, for example by a length of shrink tubing 330.

FIG. 13 is an exploded view of the sleeve and electrode slide block assembly of the embodiment shown in FIG. 10. The right sleeve slide block 292 has a projection 332 which extends inward under the right electrode slide block 284. Right sleeve connector 334 is mounted to the inner end of the projection 332, secured to the end of the proximal end of the sleeve 336. Right electrode connector 338 is attached to an inner surface of the electrode slide block 284 and is secured to the proximal end of electrode 340. The right sleeve and electrode slide blocks 292 and 284 are slidingly attached to the right friction adjustment rail 342 by screws (not shown) through slots 344 and 346, the screws being adjustable to provide sufficient friction between the blocks and the rail 342 to provide secure control over the stylet movement. The left sleeve slide block 290 and left electrode slide block 282 are mirror replicas of the right blocks and are similarly mounted on the left friction rail 344. The left sleeve and electrodes are not shown.

When the operating surgeon desires to deploy the electrodes 8 in FIG. 1 into the target tissue and the surgeon detects an obstruction in the advancement of the stylet electrode and its surrounding insulating sleeve, he or she can decide to first withdraw or retract the insulating sleeve by use of the associated slider block handle. The RF current can then be increased momentarily to the stylet electrode to heat it to a point that makes the contiguous tissue more plastic and pliable. Then the stylet can be deployed into the intervening tissue, such as a urethra. The heated stylet will pass through the urethra wall as the intervening tissue is warmed and becomes more pliable. Then, when the stylet is fully deployed into the target tissue, the applied RF current can be immediately reduced to a level to cause ablation of the target tissue. The desired effect is to raise the temperature of the affected tissue to 45° C. or more to cause internal lesions which will eventually be absorbed by the body and reduce the prostatic pressure on the urethra. Safeguards could be designed into the system to assure that the high initial RF current only lasts long enough to allow the dense or fibrous intervening tissue to be softened by the stylet electrode only long enough to permit the deployment of the stylet electrode into the target tissue. Once the stylet electrodes are positioned in the target tissue, the ablating action as set forth above and in previous applications can proceed.

Thus, when the electrodes 8 in FIG. 1 are supplied with RF current via connector 16, the electrical circuit from the stylet electrodes to a grounding plate is closed. The current density flows through the stylet electrode into the intervening tissue at deployment, and through the target tissue after stylet deployment. During the normal tissue ablation procedure, the current supplied passes through target tissues to be treated, creating lesions having the appropriate shape as seen in FIGS. 8 and 9. When two stylets are utilized, two overlapping lesions are created.

Although preferred embodiments of the subject invention have been described in some detail, it is understood that obvious variations can be made without departing from the spirit and the scope of the invention as defined by the appended claims.

We claim:

1. A method of medical treatment of a tissue mass, comprising the steps of:

a) introducing a catheter to a zone adjacent to the tissue mass to be treated, b) moving an electrically conductive flexible stylet from the catheter through a port in the catheter and through surrounding tissue into the tissue mass to be treated, c) heating the stylet to a predetermined temperature by applying RF energy to the stylet at a first level high enough to heat body tissue to facilitate passage of the stylet through the surrounding tissue, and d) further applying RF energy to the stylet at a second level high enough to kill living tissue in the mass to be treated but not high enough to immediately destroy that tissue.

2. A method for ablative treatment of a target tissue, comprising the steps of:

a) advancing an electrically conductive flexible stylet surrounded by a movable non-conductive sleeve to surrounding tissue adjacent to the target tissue, b) moving the non-conductive sleeve from a first position on the stylet to a second position on the stylet within the surrounding tissue, c) applying an electric current to the stylet to heat the stylet to a temperature sufficient to soften and make pliable contiguous tissue to facilitate the passage of the stylet through the surrounding tissue to the target tissue, d) moving the stylet through the surrounding tissue into the target tissue, and e) applying further electrical current to the stylet to heat the target tissue to a level sufficient to kill but not immediately destroy the target tissue.

3. A method for ablative treatment of target tissue, comprising the steps of:

a) advancing an electrical conductor to surrounding tissue adjacent to the target tissue, b) applying an electric current to the electrical conductor to heat the conductor to a first level sufficient to soften and make pliable contiguous tissue to facilitate the passage of the conductor through the surrounding tissue to the target tissue, c) moving the electrical conductor through the surrounding tissue into the target tissue, and d) applying further electrical current to the conductor to heat the target tissue to a level sufficient to kill but not immediately destroy the target tissue.

4. A method of medical treatment of a tissue mass, comprising the steps of:

a) introducing a catheter to a zone adjacent to the tissue mass to be treated, b) moving an electrically conductive flexible stylet from the catheter through a catheter port in the sidewall of the catheter and through surrounding tissue into the tissue mass to be treated, c) applying electromagnetic energy at a first level to the stylet to heat the stylet to a first temperature range to facilitate passage of the stylet through the surrounding tissue, and d) further applying electromagnetic energy to the stylet at a second level to heat the stylet to a second temperature to provide medical treatment to the target tissue.

5. The method of claim 4 wherein the first temperature range is sufficient to soften and make more plastic contiguous tissue, and the second temperature is lower than the first temperature range and sufficient only to kill the target tissue.

* * * * *